United States Patent [19]

Cantello et al.

[11] 4,355,004
[45] Oct. 19, 1982

[54] BENZIMIDAZOLINE DERIVATIVES AND PHARMACEUTICAL COMPOSITIONS CONTAINING THEM

[75] Inventors: Barrie C. C. Cantello, Redhill; Susan M. White, Little Bookham, both of England

[73] Assignee: Beecham Group Limited, Great Britain

[21] Appl. No.: 199,733

[22] Filed: Oct. 23, 1980

[30] Foreign Application Priority Data

Nov. 10, 1979 [GB] United Kingdom ............... 7938997

[51] Int. Cl.³ ............... A61K 31/415; C07D 233/48
[52] U.S. Cl. ............... 422/246; 424/250; 424/267; 424/248.56; 424/273 B; 548/306; 546/199; 544/62; 544/139; 544/370
[58] Field of Search ............... 544/62, 139, 370; 546/199; 548/306; 424/273 B, 248.56, 267, 250, 246

[56] References Cited

U.S. PATENT DOCUMENTS 4,182,865  1/1980  Rasmussen ............... 544/62

FOREIGN PATENT DOCUMENTS 9362  4/1980  European Pat. Off. .
11963  6/1980  European Pat. Off. .
20304  12/1980  European Pat. Off. .
1573532  8/1980  United Kingdom .

*Primary Examiner*—Robert T. Bond
*Attorney, Agent, or Firm*—Jacobs & Jacobs

[57] ABSTRACT

A compound with hypoglycaemic activity having formula (II) or a pharmaceutically acceptable ammonium or acid addition salt thereof:

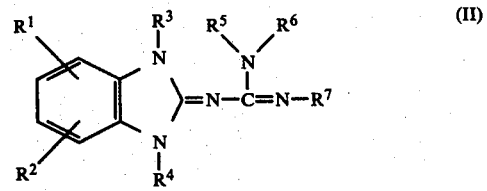

wherein
$R^1$ and $R^2$ are the same or different and represent hydrogen, $C_{1-6}$ alkyl, $C_{1-6}$ alkoxy, hydroxy or halogen;
$R^3$ and $R^4$ are the same or different and represent hydrogen or $C_{1-6}$ alkyl;
$R^5$ represents hydrogen or $C_{1-6}$ alkyl;
$R^6$ represents $C_{1-6}$ alkyl, phenyl optionally substituted with up to 3 groups selected from halogen, $C_{1-6}$ alkyl, and $C_{1-6}$ alkoxy; or benzyl optionally substituted with up to 3 groups selected from halogen, $C_{1-6}$ alkyl and $C_{1-6}$ alkoxy; or $R^5$ and $R^6$ together represent the remaining members of a 5- or 6-membered ring optionally containing an oxygen, sulphur or additional nitrogen atom and being optionally substituted with $C_{1-6}$ alkyl, carboxy or $C_{1-6}$ alkoxycarbonyl; and
$R^7$ represents phenyl, optionally substituted with up to 3 groups selected from halogen, $C_{1-6}$ alkyl and $C_{1-6}$ alkoxy, $C_{1-6}$ alkoxy carbonyl, $C_{1-6}$ alkanoyl, $C_{1-6}$ alkyanoyloxy, nitro, hydro, amino, substituted amino, and carboxy.

10 Claims, No Drawings

BENZIMIDAZOLINE DERIVATIVES AND PHARMACEUTICAL COMPOSITIONS CONTAINING THEM

This invention relates to a class of novel benzimidazoline derivatives which are useful in the treatment of diabetes. The invention also relates to a process for their preparation and to pharmaceutical compositions containing them.

The compound of formula (I):

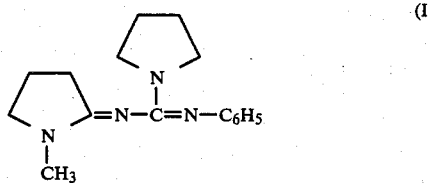

has been reported to be useful in the treatment of diabetes in Belgian Patent No. 852,565 and in Diabetes, 27, 856 and 868 (1978).

Our European Published Patent Application No. 11963 discloses a group of heterocyclic imines structurally similar to the compound of formula (I), which have hypoglycaemic activity.

We have now found a class of benzimidazoline imine compounds which have hypoglycaemic activity.

Accordingly the present invention provides a compound of formula (II) or a pharmaceutically acceptable quaternary ammonium or acid addition salt thereof:

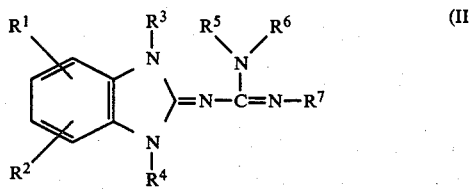

wherein $R^1$ and $R^2$ are the same or different and represent hydrogen, $C_{1-6}$ alkyl, $C_{1-6}$ alkoxy, hydroxy or halogen;

$R^3$ and $R^4$ are the same or different and represent hydrogen or $C_{1-6}$ alkyl;

$R^5$ represents hydrogen or $C_{1-6}$ alkyl;

$R^6$ represents $C_{1-6}$ alkyl, phenyl optionally substituted with up to 3 groups selected from halogen, $C_{1-6}$ alkyl, and $C_{1-6}$ alkoxy; or benzyl optionally substituted with up to 3 groups selected from halogen, $C_{1-6}$ alkyl and $C_{1-6}$ alkoxy; or $R^5$ and $R^6$ together represent the remaining members of a 5- or 6-membered ring optionally containing an oxygen, sulphur or additional nitrogen atom and being optionally substituted with $C_{1-6}$ alkyl, carboxy or $C_{1-6}$ alkoxycarbonyl; and $R^7$ represents phenyl, optionally substituted with up to 3 groups selected from halogen, $C_{1-6}$ alkyl and $C_{1-6}$ alkoxy, $C_{1-6}$ alkoxy carbonyl, $C_{1-6}$ alkanoyl, $C_{1-6}$ alkyanoyloxy, nitro, hydro, amino, substituted amino, and carboxy.

Suitable quaternary salts of compound (II) include $C_{1-6}$ alkyl halide, di-$C_{1-6}$ alkyl sulphate, and benzyl halide.

Preferred quaternary salts are the $C_{1-6}$ alkyl halides; in particular the methylhalide, such as the methyliodide salt.

Suitable acid addition salts of compound (II) include inorganic salts such as the sulphate, nitrate, phosphate and borate, hydrohalides such as the hydrochloride, hydrobromide and hydroiodide, and organic acid addition salts such as acetate, oxalate, tartrate, maleate citrate, succinate, benzoate, ascorbate, methanesulphonate and p-toluene-sulphonate.

Preferred salts are hydrohalide salts.

Examples of suitable $C_{1-6}$ alkyl groups which $R^1$ to $R^6$ may represent include methyl, ethyl, n- and iso-propyl, and n-, sec-, iso- and tert-butyl.

Suitable substituents for the phenyl and benzyl groups for $R^6$ and the phenyl group for $R^7$ include ortho-, meta- and para-methyl, methoxy, chloro and bromo.

Suitably $R^1$ and $R^2$ represent hydrogen, methyl, ethyl, or n-propyl. Preferably $R^1$ and $R^2$ are both hydrogen.

Suitably $R^3$ and $R^4$ are methyl, ethyl, n-propyl, or phenyl. Advantageously $R^3$ and $R^4$ both represent methyl.

Suitably $R^5$ is hydrogen, methyl, ethyl or n-propyl, and $R^6$ represents methyl, ethyl, n-propyl, phenyl or benzyl. When $R^5$ and $R^6$ complete a ring, suitable such rings include pyrrolidine, piperidine, morpholine, thiamorpholine, piperazine and 4-($C_{1-6}$ alkyl)piperazine, for example 4-methylpiperazine rings.

Suitably $R^7$ is phenyl.

One sub-group of compounds falling within the scope of this invention comprises compounds of formula (III) and pharmaceutically acceptable quaternary and acid addition salts thereof:

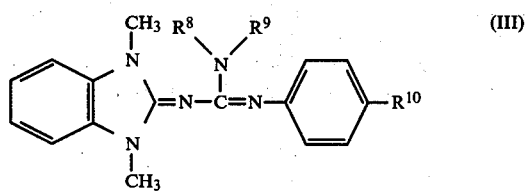

wherein $R^8$ and $R^9$ together represent the remaining members of a 5- or 6-membered ring optionally containing an oxygen, sulphur or additional nitrogen atom and being optionally substituted with $C_{1-6}$ alkyl; and $R^{10}$ represents hydrogen, $C_{1-6}$ alkyl or hydrogen.

Compounds of formula (III) include the following:
N-(1,3-dimethylbenzimidazolin-2-ylidene)-N'-phenyl-4-morpholine carboxamidine hydroiodide;
N-(1,3-dimethylbenzimidazolin-2-ylidene)-N'-phenyl-1-pyrrolidine carboxamidine hydroiodide;
N'-(4-chlorophenyl)-N-(1,3-dimethylbenzimidazolin-2-ylidene)-1-pyrrolidine carboxamidine hydroiodide;
N'-(4-chlorophenyl)-N-(1,3-dimethylbenzimidazolin-2-ylidene)-4-morpholine carboxamidine hydroiodide.

Compounds of formula (II) may be prepared by reacting a compound of formula (IV) or a salt thereof:

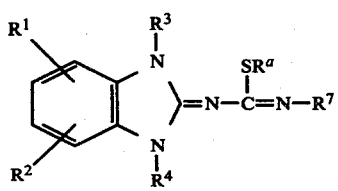 (IV)

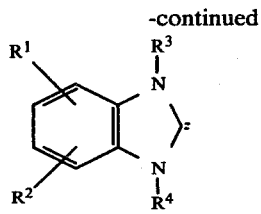 (IV)
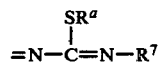

wherein $R^1$, $R^2$, $R^3$, $R^4$ and $R^7$ are as defined with respect to formula (II) above and $R^a$ represents $C_{1-6}$ alkyl; with an amine of formula $R^5R^6NH$, wherein $R^5$ and $R^6$ are as defined with reference to formula (II) above and thereafter where desired converting a free base of formula (II) so obtained into a pharmaceutically acceptable salt or converting a salt of a compound of formula (II) so obtained into the free base.

The reaction is conveniently carried out in polar organic solvent, the choice of which is not critical to the success of the reaction provided that it forms a homogeneous solution of the reagent and is substantially inert to the reagent and product. It has been found that lower alkanols such as iso-propanol are particularly convenient.

The reaction is generally carried out at a moderate temperature i.e. greater than room temperature, the reflux temperature of the solvent being selected for convenience.

The period for which the reaction is allowed to proceed depends upon the particular starting materials employed. The course of the reaction may be followed by conventional methods such as thin layer chromatography and terminated when an optimum quantity of product is present in the reaction mixture. However, in general we have found that it is convenient to leave the reaction mixture to reflux overnight.

Intermediates of general formula (IV) are novel and represent a further aspect of the invention.

Examples of lower alkyl groups which $R^a$ may represent include methyl, ethyl, n-propyl or n-butyl but preferably $R^a$ represents methyl.

The intermediates of formula (IV) may be prepared by the route shown in the following scheme:

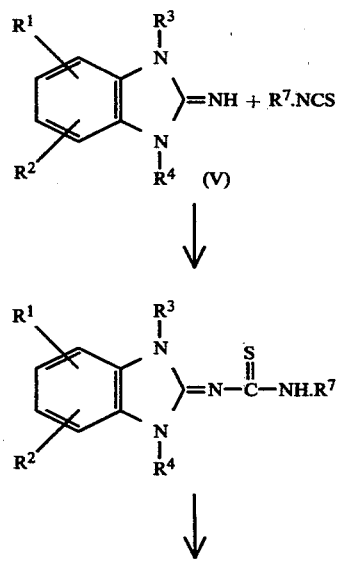

Thus, intermediates (IV) are prepared by alkylation of a thiourea (VI) using an alkylating agent $R^a.Z$ or $(R^a)_2SO_4$ wherein $R^a$ is as defined with reference to formula (IV) and Z is a leaving group such as chloride, bromide or iodide. Suitably the reaction is carried out in a polar organic solvent, the choice of which is not critical provided that the solvent is substantially inert to the reagents and product. Suitable solvents include lower alkanones and alcohols. The reaction is suitably carried out at the boiling point of the solvent.

The thiourea (VI) is in turn prepared by reacting an iso-thiocyanate $R^7.NCS$ with a corresponding imino compound (V), where $R^1$, $R^2$, $R^3$, $R^4$ and $R^7$ are as defined with reference to formula (II). This reaction is carried out in a solvent such as toluene, benzene, dioxane, tetrahydrofuran, methanol or ethanol. The reaction is carried out at non-extreme temperatures i.e. up to and including the reflux temperature of the solvent.

Compounds of formula (II) may also be prepared by reacting a compound of formula (VII).

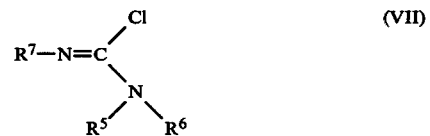 (VII)

wherein $R^5$, $R^6$ and $R^7$ are as defined with respect to formula (II) above; with an imino compound (V), where $R^1$, $R^2$, $R^3$ and $R^4$ are as defined with respect to formula (II) above and thereafter where desired converting a free base of formula (II) so obtained into a pharmaceutically acceptable salt or converting a salt of a compound of formula (II) so obtained into the free base.

The reaction is conveniently carried out in a non-hydroxylic solvent system such as an ether, chlorinated hydrocarbon or a mixture thereof. Suitable solvent systems include mixtures of diethyl ether and chloroform. The reaction is suitably carried out at ambient temperature. The period for which the reaction is allowed to proceed may be determined by methods as described hereinbefore; however, we have found it convenient to leave the reaction mixture to stand overnight.

The intermediates of formula (VII) may be prepared by reaction of an isocyanide dichloride of formula: $R^7-N=CCl_2$ wherein $R^7$ is as defined with respect to formula (II) above; with an amine of formula $R^5R^6NH$, wherein $R^5$ and $R^6$ are as defined with reference to formula (II) above. Suitably the reaction is carried out in ethereal solvent such as diethyl ether or tetrahydrofuran. The reaction is suitably carried out at ambient temperature. The period for which the reaction is allowed to proceed may be determined by methods as described hereinbefore; however we have found a two-hour reaction time to be sufficient.

The quaternary ammonium salts of compounds of formula (II) may be prepared by reaction of the compounds of formula (II) with the corresponding quaternisation agent for example ($C_{1-6}$) alkyl, or benzyl halides such as methyl iodide, ethyl bromide, propyl bromide, or benzyl chloride, or sulphuric esters e.g. di($C_{1-6}$ alkyl)sulphates such as dimethyl sulphate or diethyl sulphate. The quaternisation may be carried out in the presence or absence of a solvent, depending upon whether the quaternisation agent is or is not itself capable of acting as a solvent, at ambient temperature or under cooling, and under atmospheric pressure or under pressure in a sealed container. Organic solvents which are inert as regards the reaction and which are suitable for this purpose are ethers such as diethyl ether or tetrahydrofuran, hydrocarbons such as benzene or heptane, ketones such as acetone or butanone and $C_{1-6}$ alkanols such as ethanol, propanol or butanol. The anionic function of the quaternary salt can readily be exchanged by a traditional ion exchange technique.

In order to put the compounds (II) to use as medicinal agents for the treatment of diabetes, they are presented as pharmaceutical compositions in a variety of dosage forms. This invention therefore also includes a pharmaceutical composition which comprises a compound of formula (II) together with a pharmaceutically acceptable carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example acacia, gelatin, sorbitol, tragacanth, or polyvinylpyrrolidone; fillers, for example calcium phosphate, sorbitol or glycine; tabletting lubricants, for example magnesium stearate, talc, polyethylene glycol, or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxy-benzoate or sorbic acid, and if desired conventional flavouring or colouring agents. The compounds may also if desired be incorporated in a foodstuff, for example in the form of a biscuit.

Suppositories will contain conventional suppository bases, e.g. cocoa butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic preservative and buffering agents can be dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. The dosage employed for adult treatment will of course depend on the dose-response characteristics of the particular active ingredient but will normally be in the range 0.5 to 150 mg/kg/day.

The following Examples illustrate the preparation of a number of compounds of this invention.

EXAMPLE 1

N-(1,3-dimethylbenzimidazolin-2-ylidene)-N'-phenyl-4-morpholine carboxamidine hydroiodide (a)

1-(1,3-dimethylbenzimidazolin-2-ylidene)-3-phenyl-2-thiourea

Sodium methoxide (0.54 g) was added to a mixture of 2-imino-1,3-dimethylbenzimidazole hydroiodide (3.135 g) in ethanol (10 ml) and brought to reflux, with stirring. Phenylisothiocyanate (1.635 g) in toluene (5 ml) was added to the mixture over 10 minutes and the resulting mixture heated under reflux, with stirring, for 1 hour then cooled in ice. Filtration, washing with ethanol and water and drying gave analytically pure product, mpt 245° C.

(b)

2-Methyl-3-(1,3-dimethylbenzimidazolin-2-ylidene)-1-phenyl-2-thiopseudourea hydroiodide A mixture of 1-(1,3-dimethylbenzimidazolin-2-ylidene)-3-phenyl-2-thiourea (2.2 g) and iodomethane (1.15 g) in acetone (100 ml) was heated under reflux for 2 hours and evaporated to dryness. The residue was triturated with acetone, diluted with ether and filtered. Recrystallisation of the resultant solid from iso-propanol gave the product, mpt 199°–200°.

(c)

N-(1,3-dimethylbenzimidazolin-2-ylidene)-N'-phenyl-4-morpholine carboxamidine hydroiodide A mixture of 2-methyl-3-(1,3-dimethylbenzimidazolin-2-ylidene)-1-phenyl-2-thiopseudourea hydroiodide (3.9 g) and morpholine (3.48 g) in iso-propanol (30 ml) was heated under reflux, with stirring, for 48 hours, cooled, filtered and recrystallised from iso-propanol to give analytically pure product, mpt 247°–249°.

EXAMPLE 2

N-(1,3-dimethylbenzimidazolin-2-ylidene)-N'-phenyl-1-pyrrolidine carboxamidine hydroiodide Mpt 210°–212°, after recrystallisation from isopropanol was obtained by an analogous procedure to that described in Example 1(c), except that pyrrolidine was used in place of morpholine.

EXAMPLE 3

N'-(4-Chlorophenyl)-N-(1,3-dimethylbenzimidazolin-2-ylidene)-1-pyrrolidine carboxamidine hydroiodide

(a)

3-(4-Chlorophenyl)-1-(1,3-dimethylbenzimidazolin-2-ylidene)-2-thiourea

Mpt 232°, was prepared by an analogous precedure to that described in Example 1(a).

(b)

2-Methyl-1-(4-chlorophenyl)-3-(1,3-dimethylbenzimidazolin-2-ylidene)-2-thiopseudourea hydroiodide Mpt 195°, was prepared from 3(a) by an analogous procedure to that described in Example 1(b).

(c)

N'-(4-Chlorophenyl)-N-(1,3-dimethylbenzimidazolin-2-ylidene)-1-pyrrolidine carboxamidine hydroiodide Mpt 139°–141°, after recrystallisation from ethanol, was obtained from 2-methyl-1-(4-chlorophenyl)-3-(1,3-dimethylbenzimidazolin-2-ylidene)-2-thiopseudourea hydroiodide and pyrrolidine by an analogous procedure to that described in Example 1(c).

EXAMPLE 4

N'-(4-Chlorophenyl)-N-(1,3-dimethylbenzimidazolin-2-ylidene)-4-morpholine carboxamidine hydroiodide Mpt 205°, after recrystallisation from ethanol, was obtained from 2-methyl-1-(4-chlorophenyl)-3-(1,3-dimethylbenzimidazolin-2-ylidene)-2-thiopseudourea hydroiodide and morpholine by an analogous procedure to that described in Example 1(c).

BIOLOGICAL DATA

Activity on Glucose Tolerance in Fasted Mice

For this assay mice were fasted for 24 hours before the experiment and then randomised so that each treatment group contained 8 mice. The compounds were dosed orally in 1% aqueous carboxymethyl cellulose (10 ml/kg body weight), and 30 minutes later glucose (1 g/kg) was administered by the sub-cutaneous route. Blood samples for glucose analysis were taken from the tail 60 minutes after glucose administration; the results are shown in the table below.

N.B. A standard system for indicating the significance of results with respect to the controls (dose=zero mmol/kg) which received the 1% aqueous carboxymethyl cellulose vehicle only, is as follows:

TABLE

| Compound of Example No. | Dose mmol/kg | Blood Glucose concentration mmol/liter 60 minutes after subcutaneous glucose |
|---|---|---|
| 1 | 0 | 7.95 |
|   | 0.25 | 5.09**** |
| 3 | 0 | 7.95 |
|   | 0.25 | 3.05**** |
| 4 | 0 | 7.95 |

TABLE-continued

| Compound of Example No. | Dose mmol/kg | Blood Glucose concentration mmol/liter 60 minutes after subcutaneous glucose |
|---|---|---|
|   | 0.25 | 6.02** |

**$P < 0.05$
***$P < 0.01$
****$P < 0.001$

We claim:

1. A compound selected from the group consisting of a benzimidazoline of formula:

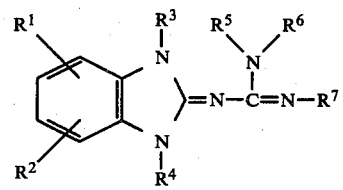

pharmaceutically acceptable acid addition salts thereof and pharmaceutically acceptable quaternary ammonium salts thereof
wherein
$R^1$ and $R^2$ are the same or different and each is hydrogen, alkyl of 1 to 6 carbon atoms, alkoxy of 1 to 6 carbon atoms, hydroxy or halo;
$R^3$ and $R^4$ are the same or different and each is hydrogen or alkyl of 1 to 6 carbon atoms;
$R^5$ is hydrogen or alkyl of 1 to 6 carbon atoms;
$R^6$ is alkyl of 1 to 6 carbon atoms, phenyl unsubstituted or substituted with up to 3 groups selected from the group consisting of halo, alkyl of 1 to 6 carbon atoms, and alkoxy of 1 to 6 carbon atoms; or benzyl unsubstituted or substituted with up to 3 members selected from the group consisting of halo, alkyl of 1 to 6 carbon atoms and alkoxy of 1 to 6 carbon atoms; or
$R^5$ and $R^6$ together with the nitrogen atom to which they are attached are pyrrolidino, piperidino, morpholino, thiamorpholino, or piperazino, unsubstituted or substituted with alkyl of 1 to 6 carbon atoms, carboxy or alkoxy-carbonyl of 1 to 6 carbon atoms; and
$R^7$ is phenyl, unsubstituted or substituted with up to 3 members selected from the group consisting of halo, alkyl of 1 to 6 carbon atoms, alkoxy of 1 to 6 carbon atoms, alkoxycarbonyl of 1 to 6 carbon atoms, alkanoyl of 1 to 6 carbon atoms, alkanoyloxy of 1 to 6 carbon atoms, nitro, hydroxy, amino and carboxy.

2. A compound according to claim 1, in which each of $R^1$ and $R^2$ is hydrogen, methyl, ethyl, n- or iso-propyl, or n-, sec-, iso- or tert butyl.

3. A compound according to claim 1 in which each of $R^3$ and $R^4$ is hydrogen, methyl, ethyl or n-propyl.

4. A compound according to claim 1 in which $R^5$ and $R^6$ together with the nitrogen to which they are attached are pyrrolidino, piperidino, morpholino, thiamorpholino, piperazino, or 4-(alkyl) piperazino, ring wherein alkyl contains from 1 to 6 carbon atoms.

5. A compound according to claim 1 in which $R^7$ is phenyl or halophenyl.

6. A compound according to claim 1 wherein said benzimidazoline is of the formula

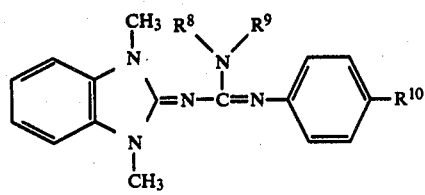

in which
R⁸ and R⁹ together with the nitrogen to which they are attached are pyrrolidino, piperidino, morpholino, thiamorpholino, or piperazino, unsubstituted or substituted with alkyl of 1 to 6 carbon atoms, and R¹⁰ is hydrogen, alkyl of 1 to 6 carbon atoms or halo.

7. A compound according to claim 1 wherein said benzimidazoline is selected from the group consisting of:

N-(1,3-dimethylbenzimidazoline-2-ylidene)-N'-phenyl-4-morpholine carboxamidine;

N-(1,3-dimethylbenzimidazolin-2-ylidene)-N'-phenyl-1-pyrrolidine carboxamidine;

N'-(4-chlorophenyl)-N-(1,3-dimethylbenzimidazolin-2-ylidene)-1-pyrrolidine carboxamidine; and N'-(4-chlorophenyl)-N-(1,3-dimethylbenzimidazolin-2-ylidene)-4-morpholine carboxamide.

8. A pharmaceutical composition which comprises an antihyperglycemic effective amount of a compound according to claim 1 in combination with a pharmaceutical carrier.

9. A composition according to claim 8 in unit dosage form.

10. A compound of the formula:

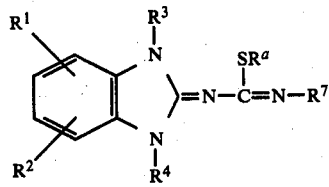

or a salt thereof wherein R¹, R², R³, R⁴ and R⁷ are as defined in claim 1 and Rᵃ is alkyl of 1 to 6 carbon atoms.

* * * * *